United States Patent [19]

Zell

[11] Patent Number: 4,752,445
[45] Date of Patent: Jun. 21, 1988

[54] BI-DIRECTIONAL SEALING METHOD TO CONTROL FLUID FLOW BETWEEN AN AIR INLET AND A PRESSURE CHAMBER

[75] Inventor: Peter E. Zell, Erie, Pa.

[73] Assignee: American Sterilizer Company, Erie, Pa.

[21] Appl. No.: 767,468

[22] Filed: Aug. 20, 1985

[51] Int. Cl.$^4$ .......................... A61L 2/06; A61L 2/16; F16K 31/145; F16K 31/165
[52] U.S. Cl. ........................................ 422/34; 422/27; 422/28; 422/33; 422/103; 422/113; 422/295; 251/61.2; 251/61.3
[58] Field of Search ................... 422/34, 33, 103, 113, 422/27, 28, 26, 295; 251/61.3, 61.2

[56] References Cited

U.S. PATENT DOCUMENTS

| | | | |
|---|---|---|---|
| 2,120,770 | 6/1938 | Stern | 251/61.3 |
| 2,158,436 | 5/1939 | Shaw | 251/61.3 |
| 3,590,859 | 7/1971 | Gotzenberger | 251/61.3 |
| 4,026,326 | 5/1977 | Wells et al. | 137/458 |
| 4,447,399 | 5/1984 | Runnells et al. | 422/27 |
| 4,457,892 | 7/1984 | Young | 422/34 |

*Primary Examiner*—David L. Lacey
*Assistant Examiner*—Lynn M. Kummert
*Attorney, Agent, or Firm*—Kirkpatrick & Lockhart

[57] ABSTRACT

A method for controlling air flow from an inlet to a chamber and from the chamber through the inlet to atmosphere wherein an ethylene oxide gas sterilization process is practiced in the chamber, which process includes conditions of controlled alternating vacuum and pressure. The method employs a diaphragm actuated two-way valve in the inlet line in combination with a remotely mounted three-way solenoid valve. The chamber is sealed against air flow during conditions of vacuum by spring biasing, and during conditions of pressure by spring and pressure biasing, a closure against an orifice in the two-way valve. The vacuum in the chamber is relieved at predetermined periods by selectively exerting sufficient fluid pressure against the diaphragm of the two-way valve to force the closure, which is operatively connected to the diaphragm, away from the orifice into an open position. The three-way solenoid valve selectively directs fluid to the diaphragm to exert fluid pressure against it and directs fluid to a location remote from the diaphragm to withdraw the fluid pressure exerted against the diaphragm.

8 Claims, 1 Drawing Sheet

BI-DIRECTIONAL SEALING METHOD TO CONTROL FLUID FLOW BETWEEN AN AIR INLET AND A PRESSURE CHAMBER

BACKGROUND OF THE INVENTION

1. Field of the Invention

The present invention involves methods for controlling fluid flow between fluid inlets and chambers, and more particularly, a method for controlling such flow to or from a pressure/vacuum chamber.

2. Description of the Prior Art

Ethylene oxide gas sterilization processes include preconditioning and exhaust phases wherein a vacuum is drawn in the sterilization chamber and a sterilizing phase wherein the goods within the chamber are exposed to ethylene oxide gas, or a mixture of ethylene oxide and freon under pressure. To provide relief from the vacuum drawn during the process, chambers are equipped with atmospheric vents. The vent must, of course, be sealed during conditions of vacuum and pressure within the chamber. During the vacuum phases, a faulty seal effects cycle efficiency and during the pressure phase, a faulty seal permits gas leakage through the vent line and into the area surrounding the chamber and thus, poses a serious safety hazard.

The conventional method of sealing chambers in which a process including controlled alternating vacuum and pressure conditions is practiced, is by providing a solenoid valve in the vent line to seal for vacuum. The solenoid valves also relieve the vacuum at predetermined electronically controlled times. The solenoid valves do not seal against both vacuum and pressure conditions, so a one-way check valve must also be placed in the vent line to seal against pressure leaks. Both the check valves and the solenoid valves, however, often present quality and reliability problems.

There are commercially available direct acting solenoid valves which can be installed back to back in opposite directions to provide sufficient flow to relieve the vacuum in smaller sterilizers. However, the use of these valves does not provide adequate flow to relieve vacuum at acceptable rates in larger units. To do so apparently requires too much electrical power and greater mass in the coil, making their use economically unfeasible for sterilization equipment.

There is a need for a method of controlling fluid flow from a fluid inlet to a chamber which permits adequate flow to relieve a vacuum in the chamber at an acceptable rate. There is a further need, especially in processes such as ethylene oxide gas sterilization, for a method of controlling fluid flow from the chamber through the inlet to atmosphere. Finally, there is a need for such a method which is economically feasible and reliable regardless of the size of the chamber.

SUMMARY OF THE INVENTION

The present invention provides a method for controlling the fluid flow between a fluid inlet line and a chamber in which a process including first periods of controlled formation of vacuum alternating with second periods of controlled formation of gas pressure conditions is practiced. The method generally includes the steps of sealing the chamber and the line against fluid flow during conditions of vacuum and pressure by biasing a closure in a closed position against an orifice, in a two-way valve within the line; and relieving the vacuum in the chamber at predetermined periods by selectively exerting sufficient pressure against the closure to counter the bias towards the closed position to move the closure into an open position away from the orifice. The method further includes the step of directing fluid pressure from a remotely mounted valve against and away from the two-way valve at the predetermined periods for selectively exerting pressure against the closure.

The method preferably includes the steps of sealing the fluid inlet line against fluid flow during first periods of vacuum by spring biasing, and during second conditions of gas pressure by spring and pressure biasing, a closure in a closed position against an orifice in a two-way valve positioned between the chamber and the inlet; relieving the vacuum in the chamber at predetermined periods by selectively exerting sufficient fluid pressure against a diaphragm in the two-way valve to force a member which operatively connects the diaphragm to the closure against the closure to overcome the spring bias to move the closure into an open position away from the orifice, wherein the open position defines sufficient space through the orifice to permit sufficient fluid flow to relieve the vacuum at a predetermined rate; and alternately directing fluid against and away from the diaphragm at the predetermined periods for selectively exerting and withdrawing fluid pressure against the diaphragm, respectively.

The step of directing fluid includes opening a first passage through a three-way valve at the predetermined periods to direct fluid from a fluid source to the diaphragm to exert fluid pressure against the diaphragm to relieve the vacuum in the chamber and closing a second passage through the three-way valve to a location remote from the diaphragm; and closing the first passage and opening the second passage during conditions of vacuum and pressure to draw away fluid exerted against the diaphragm to the remote location by providing a lower relative fluid pressure at the remote location than the fluid pressure exerted against the diaphragm.

The three-way valve is preferably a solenoid valve which may optionally include means for manually controlling the opening and closing of the passages. The fluid directed through the three-way valve may be a pressurized liquid or a pressurized gas.

The process practiced in the chamber may be an ethylene oxide sterilization process. The method of the present invention also prevents the flow of gas, such as ethylene oxide from the chamber during conditions of pressure through the inlet to atmosphere by pressure biasing the closure against the orifice in addition to the spring biasing the closure.

The method preferably employs an in line diaphragm actuated two-way valve in combination with a remotely situated three-way solenoid valve.

BRIEF DESCRIPTION OF THE DRAWINGS

The present invention can better be understood by reference to the drawings in which.

DETAILED DESCRIPTION OF THE PREFERRED EMBODIMENTS

Figure 1:
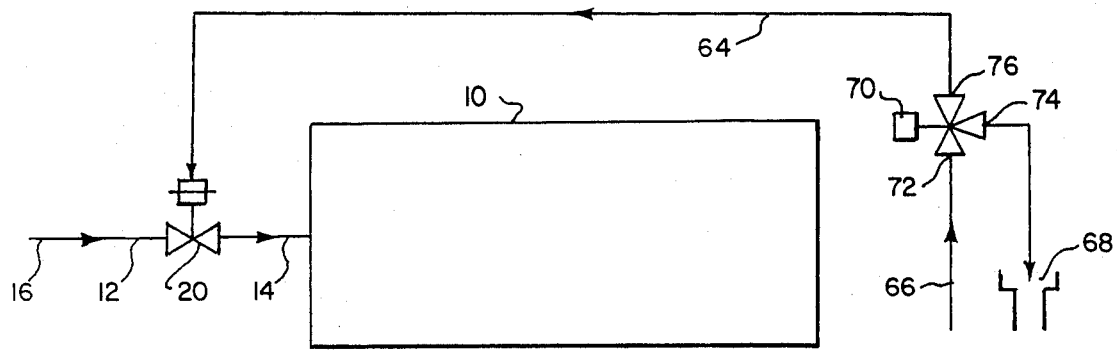
FIG. 1 is a diagrammatic view of a chamber fluidly connected to a vent line by means of a two-way valve which in turn is actuated by a three-way valve.
Figure 2:
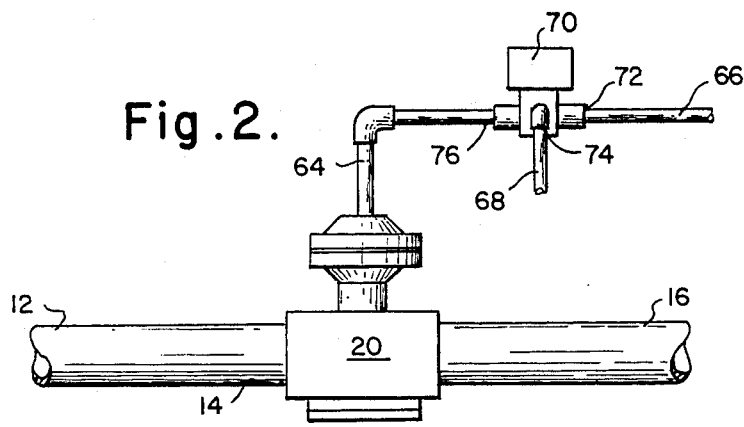
FIG. 2 is a side elevation view of the two-way valve and the three-way valve.
Figure 3:
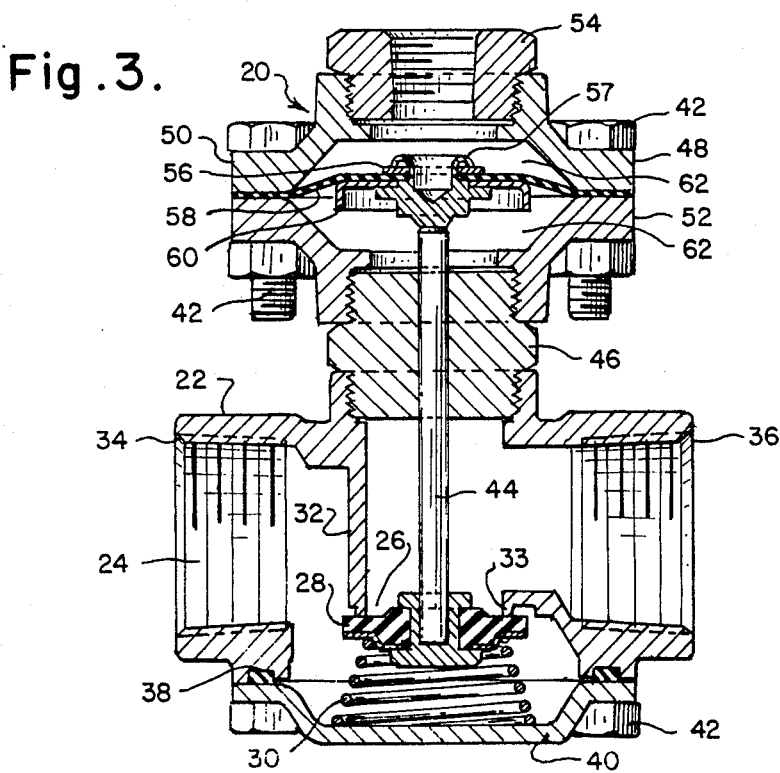
FIG. 3 is a section view of the two-way valve.

FIGS. 1 through 3 illustrate the combination of two-way and three-way valves associated with a chamber and vent line employed in the method of the present invention.

A sterilization chamber 10 includes a vent line 12 to atmosphere. Although the method and the valve assembly of the present invention are particularly well suited for use with chambers in which ethylene oxide gas sterilization processes are practiced, the method and valve assembly can be advantageous for use with any chamber in which processes which include conditions of controlled vacuum and pressure are practiced.

The valve assembly includes a two-way valve 20 and a three-way solenoid valve 70. The two-way valve 20 is positioned in the vent line 12 leading to chamber 10. The three-way valve 70 is fluidly connected to the two-way valve 20 through line 64 but remotely situated from the vent line 12.

Referring to FIG. 3, the two-way valve 20 includes a lower housing 22 and an upper housing 48. The housings may be made of metal, preferably brass. A channel 24 passes through the lower housing 22 from end 34, through orifice 26 to end 36. End 34 is connected to end 14 of vent line 12 leading to chamber 10. End 36 is connected to end 16 of vent line 12 leading to atmosphere.

A closure 28 is biased by coil spring 30 against the edge of barrier 32 and lip 33 which together define the periphery of orifice 26. Closure 28 is preferably made of a flexible elastomer having resilient properties and being resistant to the substances, such as ethylene oxide and freon, to which it is exposed.

When chamber 10 is during said second period, for example, with ethylene oxide gas, the positive pressure also biases closure 28 against orifice 26 in the closed position, thereby assuring that channel 24 is sealed against leakage of the gas into the atmosphere. The pressure biasing of closure 28 provides a fail safe mechanism for ethylene oxide gas sterilization in the event spring 30 is damaged. When, during said first periods, a vacuum is drawn in chamber 10, spring 30 alone biases closure 28 against orifice 26. Spring 30 must be structured to apply sufficient pressure against closure 28 to seal the chamber 10 against leakage from the atmosphere through vent 12 into chamber 10 to avoid destroying the vacuum. Closure 28 thus, acts as a bidirectional seal for preventing leaks to or from chamber 10 under conditions of vacuum or pressure, respectively.

Spring 30 rests on plate 40 which can be removed for service access to the valve interior. A seal 38 is positioned between plate 40 and lower housing 22. Bolts 42 secure plate 40 to housing 22.

The upper housing 48 of two-way valve 20, connected to lower housing 22 by a threaded connecting member 46, includes upper and lower portions 50 and 52, respectively, held together by bolts 42. Upper housing 48 encloses a chamber 62 wherein a diaphragm assembly 56 is located. A member 54 connects chamber 62 to line 64 and three-way valve 70.

Diaphragm assembly 56 includes a flexible rubber diaphragm 58 sandwiched between upper and lower portions 50 and 52 of housing 48 and extending through the mid portion of chamber 62 to divide chamber 62 into two distinct, separate areas. A cupped member 57 joins the diaphragm 58 to a rimmed stop 60 and actuating stem 44. Actuating stem 44 operatively connects diaphragm 58 to closure 28.

The remotely mounted three-way solenoid valve 70 includes a first port 72 leading to a fluid source 66, a second port 74 leading to a drain 68, or any suitable location remote from diaphragm 58, and a third port 76 leading to line 64 and diaphragm 58.

The vacuum in chamber 10 is relieved at predetermined times during a particular process by the application of fluid pressure through line 64 against diaphragm 58. The pressure moves diaphragm 58 down until stop 60 rests against the bottom of lower portion 52. Actuating stem 44 slides through a bore in connecting member 46 to force closure 28 away from orifice 26 into an open position. The fluid pressure exerted against diaphragm 58 must be great enough to overcome the opposing force of spring 30.

When the closure 28 is moved into the open position sufficient space is provided through orifice 26 to permit sufficient fluid flow through vent line 12 and channel 24 to relieve the vacuum in chamber 10 at a predetermined rate. For example, during an automated sterilization cycle, the vacuum drawn must be relieved at a sufficient rate to proceed with the remaining phases of the cycle in a timely manner. It is generally important in any process, and in particular sterilization, to complete the process in a timely fashion. A relatively small space through a flow control valve reduces the rate of flow and, consequently, the rate at which the chamber is returned to the desired pressure. Given a particular set of variables, such as the size of the chamber 10, the degree of negative pressure in the chamber, the time available for relieving the vacuum in a particular process, the flow rate through vent line 12 and the size of orifice 26, any particular variable can be determined. Thus, the sizes of chamber 10 and orifice 26 can be selected to break the vacuum at a specific predetermined rate suitable to the process to be practiced in chamber 10.

The three-way valve 70 is electrically powered to selectively direct fluid flow at the predetermined periods during which it is necessary to exert or withdraw pressure from diaphragm 58. Means for manually controlling valve 70 may optionally be provided. In the sterilizer application, the fluid source 66 may be pressurized water employed in the sterilizer system. In other applications, the fluid of choice may be compressed air.

When the three-way solenoid valve 70 is in a nonenergized state, the water from source 66 is blocked at port 72. Ports 74 and 76 are open to fluidly connect line 64 to the drain 68. When solenoid valve 70 is electrically energized, port 74 is closed and ports 72 and 76 are opened to fluidly connect the source 66 to line 64. Fluid from source 66 is directed through line 64 to the portion of chamber 62 above diaphragm 58 to exert fluid pressure against diaphragm 58 to move closure 28 into the open position. As long as there is a signal to solenoid valve 70, the fluid pressure exerted against diaphragm 58 will continue so that closure 28 is maintained in the open position as long as needed.

When the signal is dropped, port 72 is closed and ports 74 and 76 are opened. The fluid in line 64 and chamber 62 is drawn towards drain 68 which has a lower relative pressure than the pressure exerted against diaphragm 58. As the actuating stem 44 exerts less force against closure 28, the force of spring 30 again moves closure 28 into the closed position against orifice 26, thereby sealing chamber 10.

The method of the present invention employs the valve assembly described above to control the air flow from the vent line 12, or any fluid inlet, to chamber 10. According to the method, the chamber 10 is sealed against fluid flow during conditions of vacuum by spring biasing closure 28 in the closed position against orifice 26 in valve 20. During conditions of pressure, the chamber 10 is sealed against fluid flow by spring and pressure biasing closure 28 in the closed position. The vacuum in chamber 10 is relieved at predetermined periods (depending on the particular process requirements) by selectively exerting sufficient fluid pressure against diaphragm 58 to force the actuating stem 44 downwardly against closure 28 to overcome the upward bias exerted by spring 30 against closure 28. The downward force of actuating stem 44 moves closure 28 away from orifice 26 into the open position. The method further includes the step of alternately directing fluid against or away from diaphragm 58 at predetermined periods for selectively exerting or withdrawing pressure against diaphragm 58, respectively.

In the preferred embodiment of the valve assembly, the fluid directing step employs the three-way solenoid valve 70, by any suitable means for directing sufficient fluid pressure at the predetermined process periods to actuate the stem 44 to open closure 28 can be employed.

What is claimed is:

1. A method for controlling the fluid flow through a vent from a fluid inlet from atmosphere to a chamber in which a process including first periods of controlled formation of vacuum conditions alternating with second periods of controlled formation of pressure conditions in said chamber is practiced, comprising the steps of:

sealing said vent against fluid flow therethrough during said first periods of vacuum by spring biasing, and during said second periods of pressure by spring and pressure biasing, of a closure in a closed position against an orifice in a two-way valve which is positioned in said vent between said chamber and said fluid inlet;

opening said vent to relieve a vacuum formed in said chamber during said first periods at predetermined periods by selectively exerting sufficient control fluid pressure against a diaphragm in said two-way valve to force a member which operatively connects said diaphragm to said closure against said closure to overcome the spring bias to move said closure into an open position away from said orifice, said open position defining sufficient space through said orifice to permit sufficient fluid flow to relieve the vacuum formed in said chamber during said first periods at a predetermined rate, said step of selectively exerting sufficient control fluid pressure during said predetermined periods comprising:

directing a control fluid against said diaphragm during said predetermined periods to selectively exert control fluid pressure against said diaphragm, said control fluid directing step comprising:

opening a first passage through a three-way valve connected to a control fluid line which is in flow communication with an inlet of said two-way valve adjacent said diaphragm at said predetermined periods to direct control fluid from a control fluid source in flow communication with said three-way valve to said diaphragm to exert control fluid pressure against said diaphragm to relieve the vacuum formed in said chamber during said first periods and closing a second passage through said three-way valve which places said inlet of said two-way valve in flow communication with a location remote from said diaphragm;

during said first and second periods, directing control fluid away from said diaphragm to relieve control fluid pressure on said diaphragm by closing said first passage and opening said second passage to draw away control fluid directed against said diaphragm to said remote location by providing a lower relative control fluid pressure at said remote location than the fluid pressure exerted against said diaphragm.

2. The method recited in claim 1 wherein the opening and closing of the passages of said three-way valve is controlled electrically.

3. The method recited in claim 1 wherein the opening and closing of the passages of said three-way valve is manually controlled.

4. The method recited in claim 1 wherein said process practiced in said chamber is an ethylene oxide sterilization process.

5. A method for controlling the gas flow through a vent from an inlet from atmosphere to a chamber, wherein an ethylene oxide gas sterilization process, including first periods of controlled formation of vacuum conditions alternating with second periods of controlled formation of gas pressure conditions, is practiced in said chamber, the method comprising the steps of:

sealing said vent against gas flow therethrough during said first periods of vacuum by spring biasing, and during said second periods of gas pressure by spring and pressure biasing, of a closure in a closed position against an orifice in a two-way valve which is positioned in said vent between said chamber and said inlet;

opening said vent to relieve a vacuum formed in said chamber during said first periods at predetermined periods by selectively exerting sufficient control fluid pressure against a diaphragm in said two-way valve to force a member operatively connected to said diaphragm against said closure to overcome the spring bias to move said closure into an open position away from said orifice, said open position defining sufficient space through said orifice to permit sufficient gas flow to relieve the vacuum formed in said chamber during said first periods at a predetermined rate, said step of selectively exerting sufficient control fluid pressure during said predetermined periods comprising:

directing a control fluid against said diaphragm during said predetermined periods to selectively exert control fluid pressure against said diaphragm, said control fluid directing step comprising:

opening a first passage through a three-way valve connected to a control fluid line which is in flow communication with an inlet of said two-way valve adjacent said diaphragm at said predetermined periods to direct control fluid from a control fluid source in flow communication with said three-way valve to said diaphragm to exert control fluid pressure against said diaphragm to relieve the vacuum formed in said chamber during said first periods and closing a second passage through said three-way valve which places said inlet of said two-way valve in flow communication with a location remote from said diaphragm;

during said first and second periods, directing control fluid away from said diaphragm to relieve control fluid pressure on said diaphragm by closing said first passage and opening said second passage to draw away control fluid directed against said diaphragm to said remote location by providing a lower relative control fluid pressure at said remote location than the fluid pressure exerted against said diaphragm.

6. The method recited in claim 5 wherein said control fluid is a pressurized liquid.

7. The method recited in claim 5 wherein said control fluid is a pressurized gas.

8. The method recited in claim 5 wherein said three-way valve is a solenoid valve and wherein means for manually controlling said solenoid valve to selectively open and close said first and second passages are operatively associated with said solenoid valve.

* * * * *

UNITED STATES PATENT AND TRADEMARK OFFICE
CERTIFICATE OF CORRECTION

PATENT NO. : 4,752,445
DATED : June 21, 1988
INVENTOR(S) : Peter Edward Zell

It is certified that error appears in the above-identified patent and that said Letters Patent is hereby corrected as shown below:

Col. 3, line 36, after "is", insert --pressurized--.

Signed and Sealed this

Twenty-fourth Day of January, 1989

Attest:

DONALD J. QUIGG

Attesting Officer      Commissioner of Patents and Trademarks